United States Patent [19]
Swisher

[11] Patent Number: 5,531,695
[45] Date of Patent: Jul. 2, 1996

[54] TAMPER EVIDENT SLEEVE

[75] Inventor: David R. Swisher, Maryland Heights, Mo.

[73] Assignee: Sherwood Medical Company, St. Louis, Mo.

[21] Appl. No.: 362,704

[22] Filed: Dec. 22, 1994

[51] Int. Cl.$^6$ .................................................. A61M 5/00
[52] U.S. Cl. ........................... 604/111; 604/283; 604/905
[58] Field of Search .................................... 215/247, 249, 215/251; 604/111, 244, 250, 283, 905

[56] References Cited

U.S. PATENT DOCUMENTS

| | | |
|---|---|---|
| 4,286,640 | 9/1981 | Knox et al. . |
| 4,340,052 | 7/1982 | Dennehey et al. .................. 128/247 |
| 4,402,691 | 9/1983 | Rosenthal et al. . |
| 4,405,312 | 9/1983 | Gross et al. ........................ 604/29 |
| 4,473,369 | 9/1984 | Lueders et al. . |
| 4,631,056 | 12/1986 | Dye .................................... 604/111 |
| 4,693,707 | 9/1987 | Dye . |
| 4,723,948 | 2/1988 | Clark et al. . |
| 4,834,706 | 5/1989 | Beck et al. . |

*Primary Examiner*—Corrine M. Maglione
*Assistant Examiner*—N. Kent Gring
*Attorney, Agent, or Firm*—Montgomery W. Smith; Ari M. Bai

[57] ABSTRACT

A sleeve which includes a tamper-evident indicator that is securely engagable to a catheter assembly and allows for clear visual indication of whether the connected tubes have been tampered with or the tubes have been disconnected and reconnected. The sleeve comprises a first and second cover portions having a hollow cylindrical shape including barb members attached to the interior surface of the cover portions. A tab connects the two cover portions and is severable from the catheter assembly upon pulling the tab relative to the cover portions, thereby releasing the sleeve. Other than by using the tab, a user cannot release the sleeve without an indication of tampering to the sleeve itself.

7 Claims, 6 Drawing Sheets

TAMPER EVIDENT SLEEVE

BACKGROUND OF THE INVENTION

1. Field of the Invention

This invention relates to tamper evident devices and more particularly to the tamper evident devices at the juncture of interconnected sections of medical fluid conduits to provide an indication that the sections have or have not been disconnected and then reconnected.

2. Prior Art

Human body fluid drainage systems, such as urine collection systems, often include a catheter, such as a Foley catheter, having its distal end disposed in the bladder of a patient and its proximal end connected to a tube connector of a drainage tube which connects the catheter with a urine collection container or bag.

Such Foley catheters are often maintained in position in a hospitalized patient and connected to the drainage bag for substantial periods of time. To avoid patient infections, such components are sold in a sterile condition. However, since the components are usually packaged and sold separately, there is a danger of bacteria entering the urine drainage system upon assembly and connection of the catheter to the drainage tube for use, this bacteria could thereafter cause a urinary tract infection in the patient. To avoid the possibility of bacteria entering the system at the time of connection of the catheter tube and drainage tube, some manufacturers preconnect the catheter and drainage tube with the tube connector at the factory, sterilize the preconnected system, and package and sell the system in the assembled condition.

However, certain hospital requirements necessitate the disconnection and reconnection of the catheter and drainage tube of urine collection systems such as when a replacement bag is required or bladder irrigation is desired without the removal of the original catheter from the patient. Additionally, patients are sometimes motivated to disconnect the drainage bag and tube from the catheter without authorization for reasons of patient mobility, convenience, comfort or the like. It is, of course important to hospital personnel to know if the system has been tampered with or if disconnection and reconnection has occurred, whether or not such was for an authorized purpose. For example, when monitoring or measuring urine drainage, it is necessary to know if there has been a disconnection of the urine collection container from the catheter in order to have confidence in the determination of total volume or urine passed by the patient.

In order to provide an assured indication that the catheter has or has not been disconnected and reconnected, a tamper-evident seal has been suggested. For example, U.S. Pat. No. 4,194,509 to Pickering et al proposes a tamper-evident shrink wrap which seals the juncture of the catheter and drainage tube prior to sterilization. This heat shrinkable wrap of Pickering et al consists of a length of heat shrinkable adhesive tape and a circumferentially extending tear strip made of a shrinkable resin, for example, a polyolefin such as a polyethlene. In order to apply this wrap material, a heat source must be used to shrink the wrap around the connection between the tubes. This tends to complicate the overall manufacture and assembly of the preconnected system and also does not allow for the medical user to assemble the tamper-evident seal at the patient bedside. After the tamper-evident seal of Pickering et al is in position, it conceals the juncture of the tube connector and the drainage tube, thereby making it difficult to subsequently ascertain that a proper, fluid-tight engagement exists between these elements. In order to disconnect these elements for any purpose, a tear strip located on the heat shrink seal of Pickering et al must be located, gripped and tangentially pulled away from the seal to tear a portion of the wrap away from the tube connector. It is sometimes not readily apparent however from the smooth band of wrap remaining around the connector that the connection between the catheter and drainage tube has been compromised.

BRIEF SUMMARY AND OBJECT OF THE INVENTION

In brief summary, the present invention overcomes and substantially alleviates the deficiencies in the prior art by providing a tamper evident sleeve which is securely engagable to a pair of tubular sections joined by a tube connector and allows for clear visual indication of whether the connection has been tampered with or the tubes have been disconnected and reconnected.

Accordingly, it is a principle object of the present invention to provide an improved tamper-evident sleeve securable about a tube connection wherein one or more of the above mentioned problems or disadvantages is overcome.

Another object of the present invention is to provide an improved tamper-evident sleeve for a tube connection which is easy to apply during assembly, is constructed of economical material, provides an obvious and continuing indication that the tubes have or have not been disconnected, and does not hinder or complicate in any way the disconnection of the tubes for legitimate purposes.

Another further object of the present invention is to provide a tamper-evident sleeve which can be attached and removed from the connected tubes by the medical user at the patient bedside.

These and other objects of the present invention are realized in a presently preferred embodiment thereof, described by way of example and not necessarily by way of limitation, which provides a tamper-evident sleeve for use with a tube connector for providing evidence of tampering with the connection of two tubes. The tamper-evident sleeve includes opposed cover portions that encircle and lock around the tube connector. The sleeve includes a severable, axially extending peel tab located between the cover portions of the sleeve which has a width substantially less than the circumference of the tube connector.

Additional objects, advantages and novel features of the invention will be set forth in the description which follows, and will become apparent to those skilled in the art upon examination of the following more detailed description, along with the accompanying drawings in which like elements of the invention are similarly numbered throughout.

DETAILED DESCRIPTION OF THE ILLUSTRATED EMBODIMENT

Figure 1:
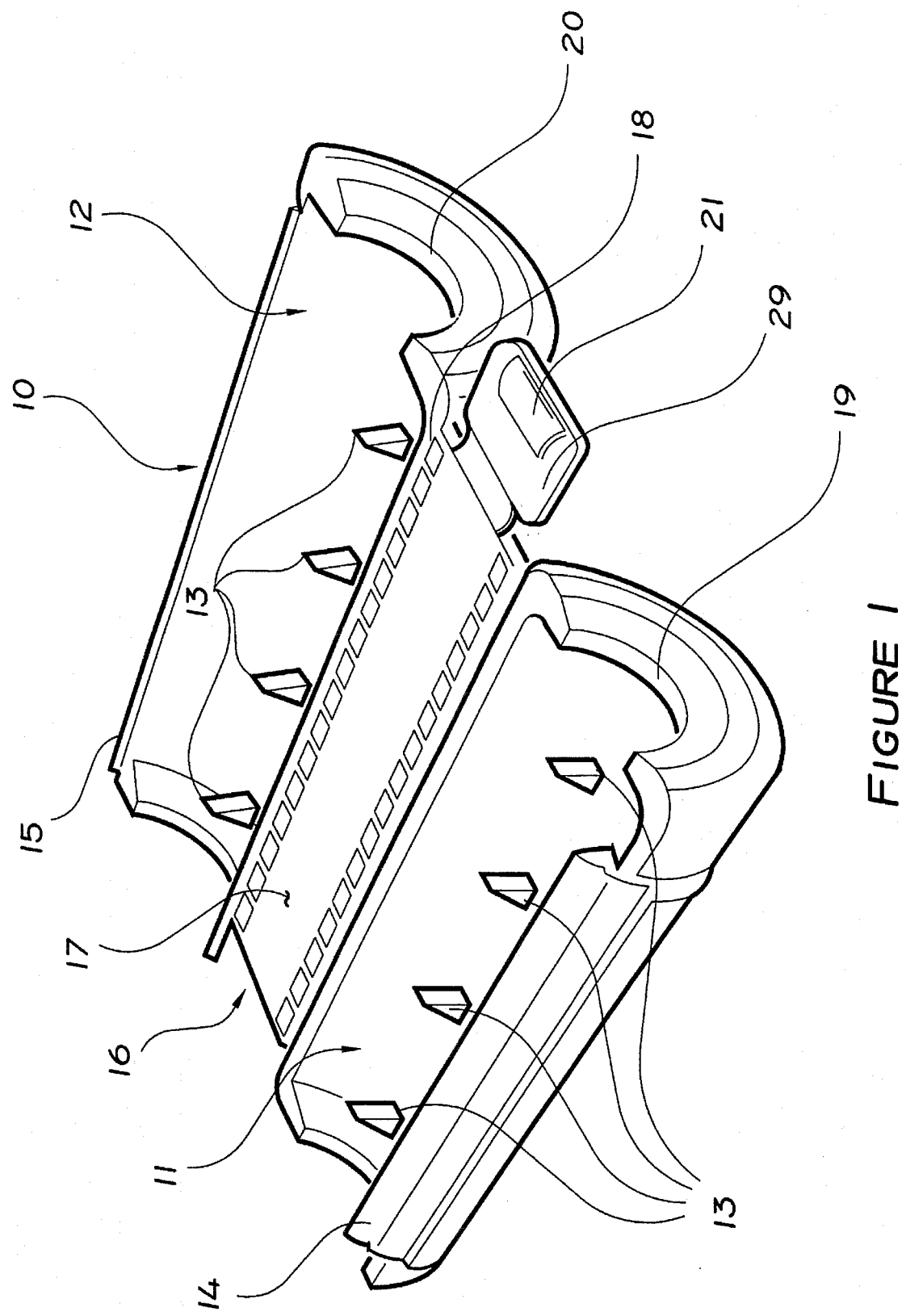
FIG. 1 is a perspective view of a tamper-evident sleeve made in accordance with the principles of the present invention shown in its open position.

Referring now in more detail to the drawings, and more particularly to FIG. 1, the tamper-evident sleeve 10 is shown in the open position prior to its attachment to a conventional Foley catheter assembly (not shown) of a urinary drainage system (also not shown). The sleeve 10 includes a first cover portion 11 and second cover portion 12 with each portion having a hollow semi-cylindrical shape. Cover portions 11 and 12 include a plurality of barb members 13 attached to the interior surface thereof in two straight lines that run from the proximal end to the distal end of each cover member 11 and 12. The outer edge of the first cover portion 11 has a male clasp member 14 which is connectable to a female clasp member 15 located at the outer edge of the second cover portion 12.

Located at the distal end of each cover member 11 and 12 is a first collar 19 and second collar 20 respectfully. Each collar 19 and 20 forms a semi-cylindrical opening when the sleeve 10 is in the open position as illustrated in FIG. 1. When the sleeve 10 is in the closed and locked position, the collars 19 and 20 form an annular opening which secures the sleeve 10 to the neck 26 (see FIG. 6) of the Foley catheter connector.

Interposed between the inner edges of the first and second cover portions 11 and 12 is a peel tab 16. The peel tab 16 includes a severing member 17 which is interposed along and runs parallel with the entire length of the inner edge of the first and second cover portions 11 and 12. The severing member 17 is attached to the first and second cover portions 11 and 12 by a plurality of severable ribs 18 located on both sides of the severing member 17. Each rib 18 is formed as a thin strip between the severing member 17 and each of the cover portions 11 and 12 and is preferably composed of polyethylene or polypropylene or any other suitable elastomeric material which allows for easy separation of the severing member 17 from the cover portions 11 and 12 when sufficient axial force is exerted on the ribs 18. The ribs 18 are attached at an acute angle to the severing member 17 with respect to the cover portions 11 and 12 in order to exert greater axial force on the ribs 18 when being severed.

Attached to the distal end of the severing member 17 is finger tab 29 which forms a rectangular shape. The finger tab 29 further includes a gripping member 21 located at the distal end of both sides of finger tab 29 and is preferably shaped as a semi-cylindrical bump which facilitates gripping between the a user's thumb and finger.

Figure 2:
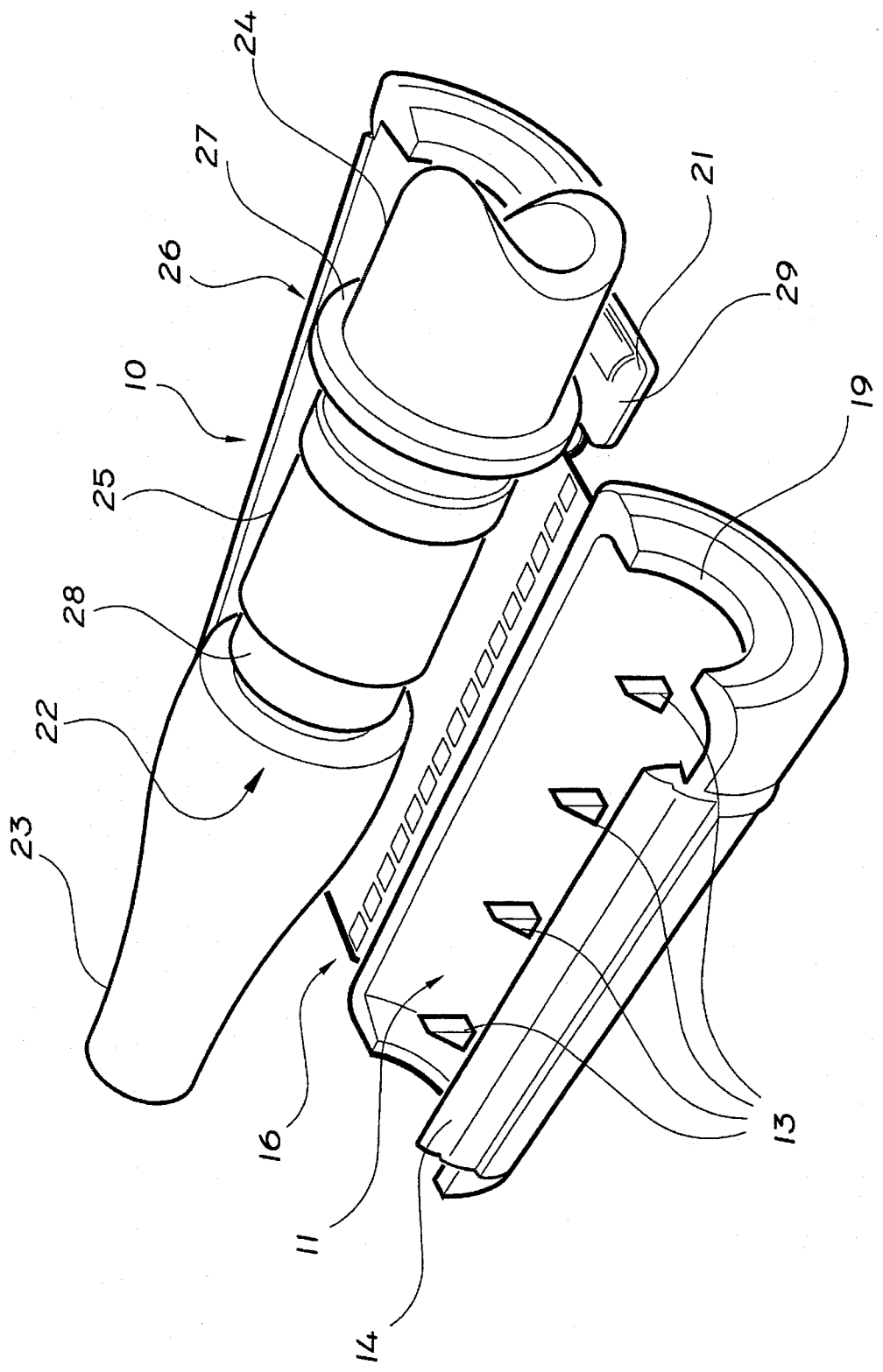
FIG. 2 is a perspective view of the preferred embodiment of the invention shown with the tamper-evident sleeve thereof in the open position ready for attachment about a pair of tubes attached with a tube connector.

Reference is now made to FIG. 2 which shows the sleeve 10 in the open position with the Foley catheter assembly 22 disposed therein. The Foley catheter assembly 22 conventionally includes a Foley catheter 23, a drainage tube 24, and a tube connector 25 interposed therebetween for interconnecting the catheter 23 and the tube 24 in fluid tight engagement.

The connector of the assembly 22 may be of any known style suitable for coupling the catheter 23 to the drainage tube 24, however in the in the preferred embodiment, the tube connector 25 includes a neck 26 that has a flange 27 at its distal end which engages and securely connects the proximal end of the drainage tube 24 to the connector 25. The tube connector 25 further includes a decreasingly stepped proximal end 28 for securely receiving the catheter 23 in fluid tight engagement with the connector 25.

Figure 3:
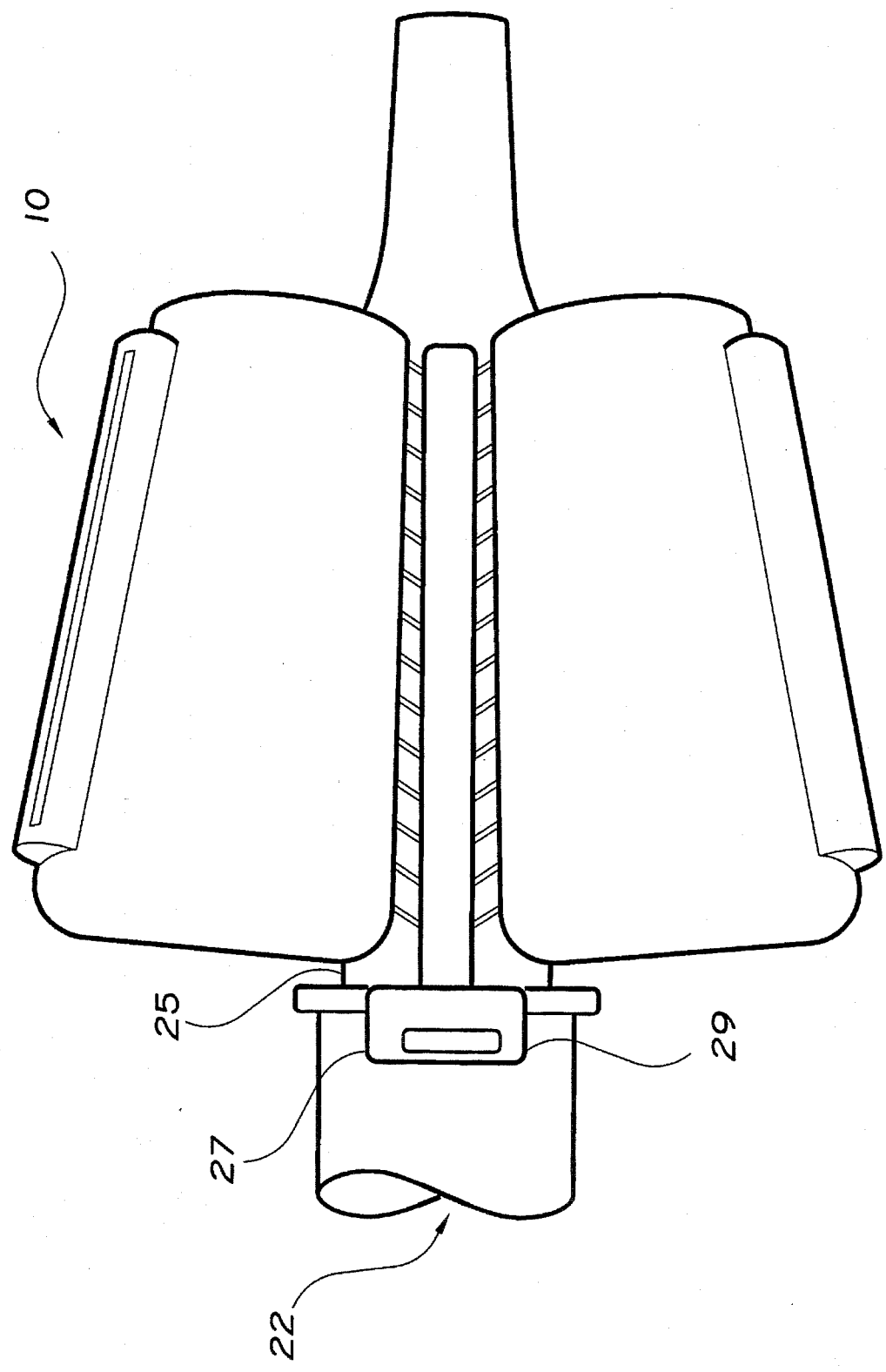
FIG. 3 is a bottom perspective view of the invention showing the tamper-evident sleeve thereof in the open position.

Referring now to FIG. 3, the method of securing the sleeve 10 to the Foley catheter assembly 22 shall be described in greater detail. Initial attachment of sleeve 10 onto the assembly 22 requires placing the sleeve so that it covers all but the flange 27 of the tube connector 25 with the tab portion 29 being directly above the flange 27 once the sleeve 10 is in the locked position.

Figure 4:
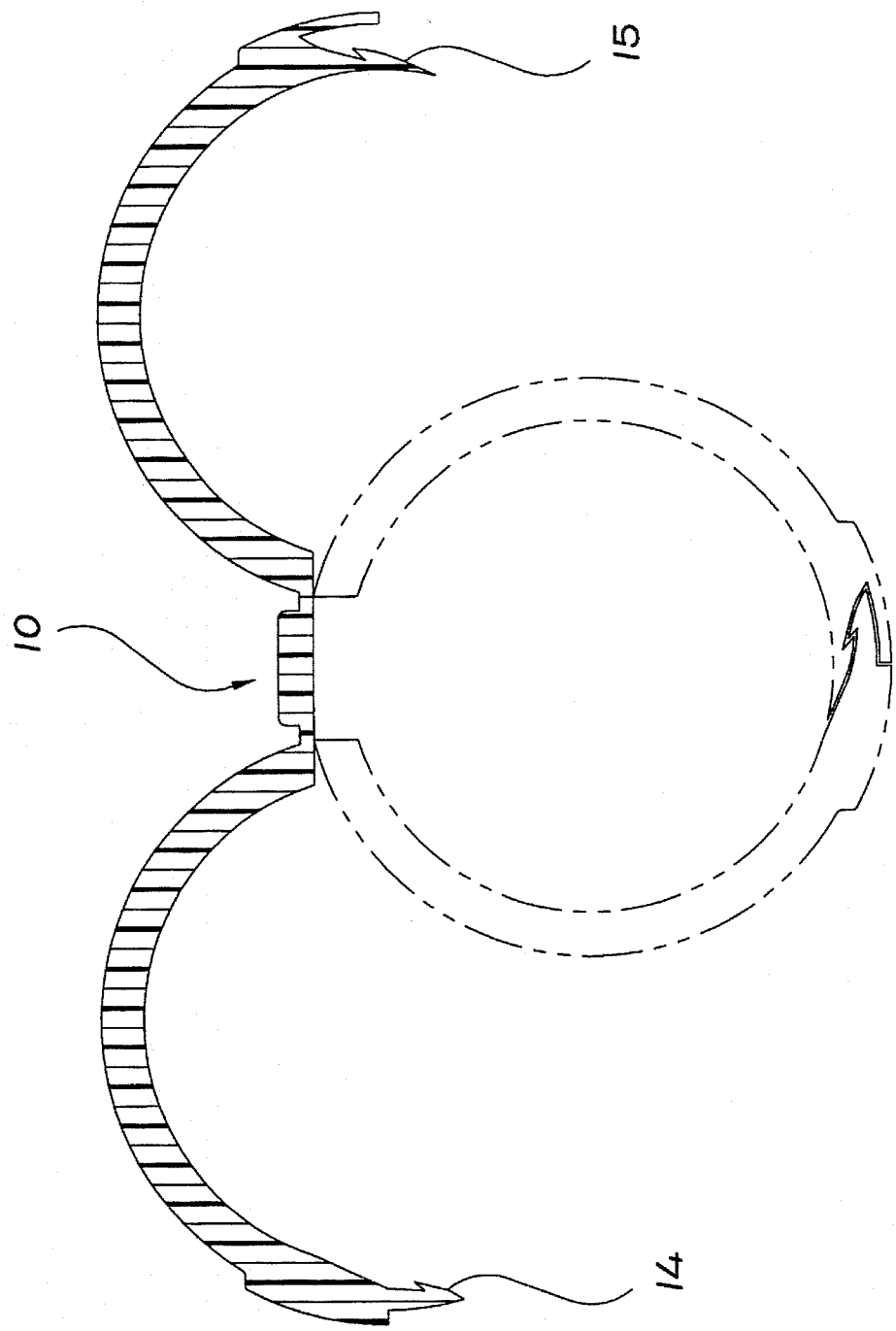
FIG. 4 is an front cross section view of the tamper-evident sleeve of the invention shown in the open position in solid line and in the closed position in phantom lines.

FIG. 4 is a front end profile of the sleeve 10 showing the sleeve 10 in solid line in the open position and in phantom line in the closed position. When the medical user places the sleeve 10 in the locked position, both the male clasp member 14 and the female clasp member 15 are brought together around the Foley catheter assembly 22 (see FIG. 6) until both clasp members 14 and 15 are securely engaged in the locked position around the tube connector 25.

Figure 5:
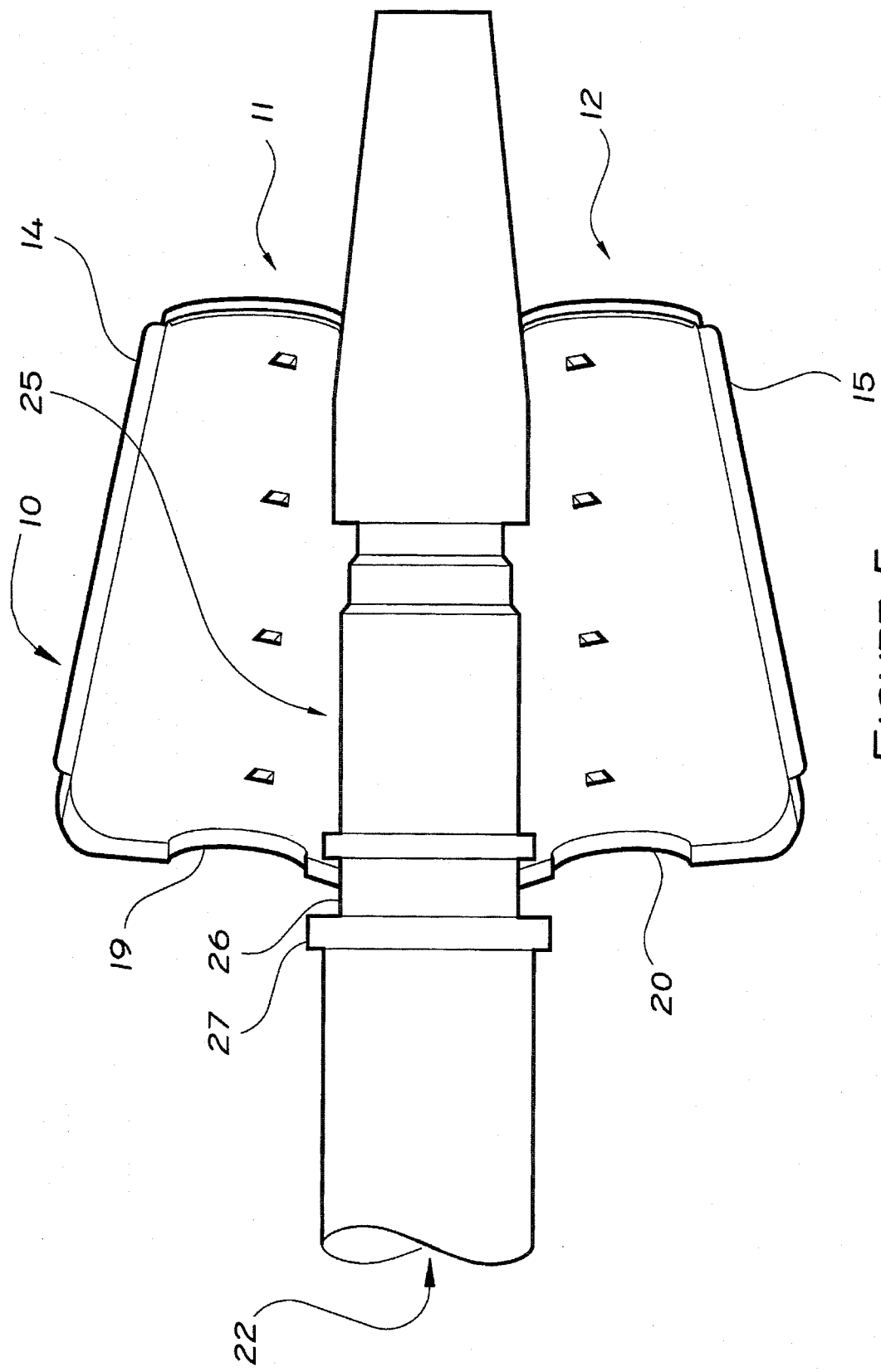
FIG. 5 is a top perspective view of the invention showing the tamper-evident sleeve thereof in the open position.

Referring now to FIG. 5, the flange 27 of the tube connector 25 is shown with the sleeve 10 in the open position. The collars 19 and 20 of sleeve 10 are designed to fit securely around the neck 26 of the tube connector 25 when the sleeve 10 is placed in the locked position.

Figure 6:
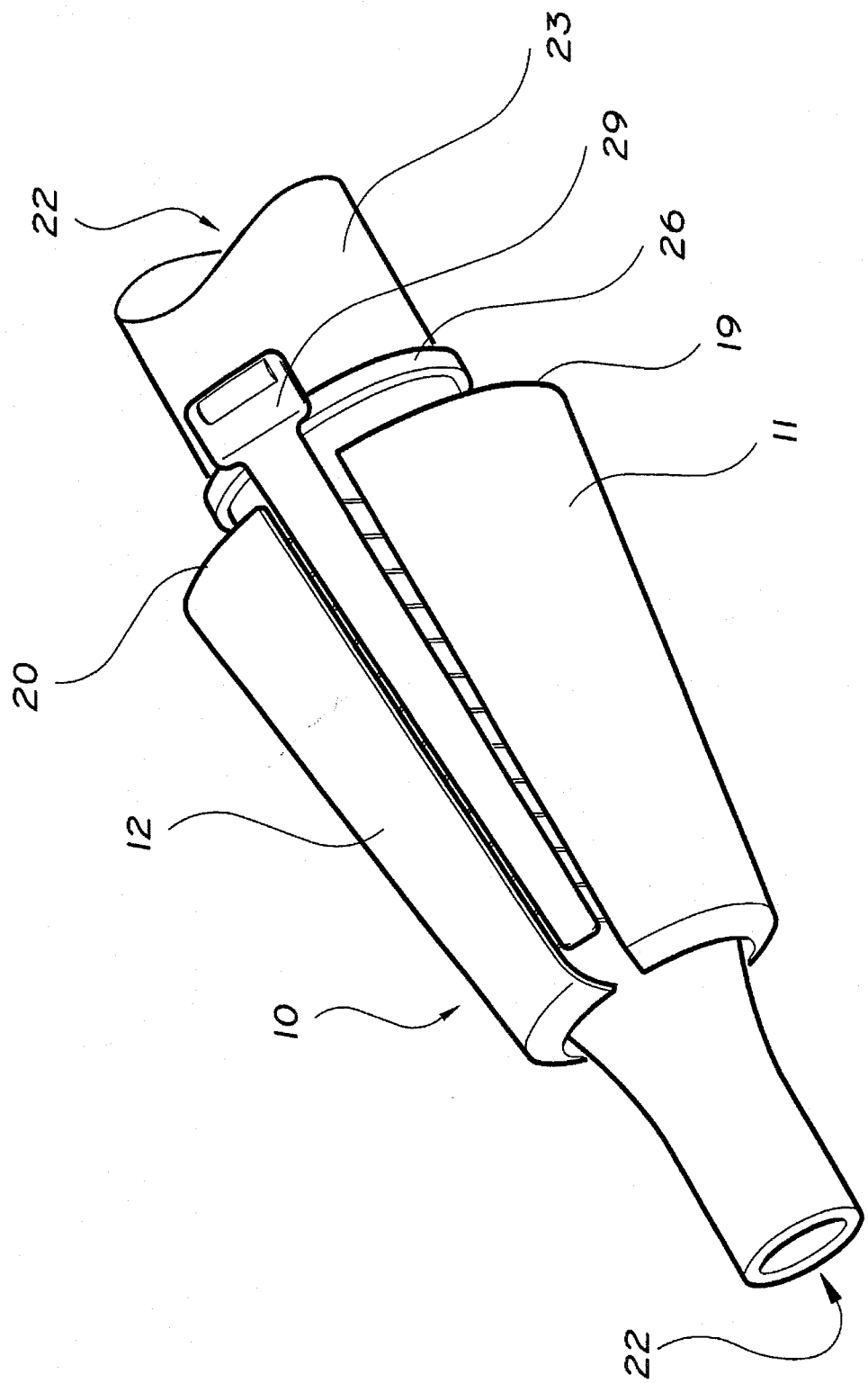
FIG. 6 is a perspective view of the invention with the tamper-evident sleeve closed about the tube connector.

In the locked position, as shown in FIG. 6, the collars 19 and 20 of both the first and second cover portions 11 and 12 respectfully, lock around the neck 26 of the tube connector 25 so that the flange 27 of neck 26 is left exposed and prevents the sleeve 10 from being pulled off in the distal direction due to the flange 27 blocking the translational movement of sleeve 10. Further, when the sleeve 10 is brought into the locked position, the barb members 13 impinge the elastomeric material of the catheter 23 of assembly 22 to assist in securely engaging the sleeve 10 to the tube connector 25. The engagement of the barb members 13 further prevents removal of the catheter 22 because any attempt to remove the sleeve 10 from the connector 25 without destroying the sleeve 10 will cause the barb members 13 to rip the elastomeric material of the catheter. Thus, an unauthorized removal of the sleeve 10 by either an attempt to pull the sleeve 10 off the connector 25 or to remove the catheter 22 from the connector 25 without first tearing the severing member 17 will give a clear indication that the sleeve 10 has been tampered with. Authorized removal of sleeve 10 may be accomplished by simply gripping the finger tab 29 of the peel tab 16 and pulling in an axial direction relative to the sleeve 10. The force of the pulling action toward the proximal end of the sleeve 10 will sever the plurality of ribs 18 connected between the severing member 17 and the first and second cover portions 11 and 12, thereby releasing the sleeve 10 from the assembly 22.

Should it be desired, a time-line indicator may also be employed with the sleeve 10 in the form of different color sleeves 10 in order to show a particular day of the week. Employment of such a color scheme will give further indication of tampering in that different sleeves 10 of the same color could be avoided in replacing an already attached sleeve 10 so as to inform medical personnel of the age of the sleeve presently in use.

Although particular embodiments of the invention have been shown, it is not intended that the invention be limited thereby, instead, the scope of the present invention is intended to be limited only by the appended claims.

I claim:

1. A tamper-evident sleeve in combination with a tube connector that joins a first tube and a second tube, said first and second tubes each having an exterior surface and said tube connector having a distal end connected to said second tube, said sleeve comprising:

a first cover portion, a second cover portion and a peel tab, said first and second cover portions each forming a hollow semi-cylindrical shape and each having an interior surface, and being joined to each other by said peel tab;

said first and second cover portions each have a plurality of barbs attached to the interior surfaces of said cover portions, said peel tab having a proximal end and a distal end; and, each of said first and second cover portions further including first and second clasp portions respectively which are interattachable to lock said cover portions into a closed position about said tube connector, whereby said peel tab is tearable and severable from said first and second cover portions.

2. The combination according to claim 1, wherein when said first and second cover portions are in said locked position around said tube connector, said barbs pinch the exterior surface of at least one of the joined tubes, thereby inhibiting separation of the joined tubes from said tube connector.

3. The combination according to claim 1, wherein when said first and second cover portions are in said locked position around said tube connector, said barbs penetrate the exterior surface of at least one of the joined tubes, thereby inhibiting separation of the joined tubes from said tube connector.

4. The combination according to claim 1, wherein said peel tab includes a finger tab at its distal end and a severing member positioned between said first and second cover portions.

5. The combination according to claim 4, wherein said severing member is attached to said first and second cover portions by a plurality of severable ribs.

6. The combination according to claim 5, wherein said plurality of severable ribs are placed at an acute angle relative to said severing member.

7. The combination according to claim 1, wherein said tube connector includes a neck at its distal end and said sleeve includes a collar interengagable with said neck when said sleeve is in said locked position.

* * * * *